United States Patent [19]

Samejima et al.

[11] Patent Number: 5,202,129
[45] Date of Patent: Apr. 13, 1993

[54] PROCESS FOR MICRONIZING SLIGHTLY-SOLUBLE DRUG

[75] Inventors: Masayoshi Samejima, Mino; Kazuo Noda, Takarazuka; Masao Kobayashi, Kyoto; Takashi Osawa, Toyonaka, all of Japan

[73] Assignee: Tanabe Seiyaku Co., Ltd., Osaka, Japan

[21] Appl. No.: 563,091

[22] Filed: Aug. 3, 1990

[30] Foreign Application Priority Data

Aug. 4, 1989 [JP] Japan .................... 1-204132

[51] Int. Cl.$^5$ .................... A61K 9/14; A61K 9/16
[52] U.S. Cl. .................... 424/489; 424/47; 424/451; 424/464
[58] Field of Search .......... 424/440, 441, 465, 464, 424/47, 451

[56] References Cited

U.S. PATENT DOCUMENTS 4,753,800  6/1988  Mozda .................... 424/440

FOREIGN PATENT DOCUMENTS 2108032 12/1972 France .
2162245  7/1973 France .
2257256  8/1975 France .
32718/76 3/1976 Japan .
9315/78  1/1978 Japan .
8220/85  1/1985 Japan .
2159407 12/1985 United Kingdom .
2224207  2/1990 United Kingdom .

OTHER PUBLICATIONS

Remingtons Pharmaceutical Sciences, 1988 Edition Mack Publishing Co.
"Optimization of In Vitro Availability of Diazepam" by S. Leucuta et al., Clujul Medical 1982, vol. LV-No. 1.
"Properties and Dissolution of Drugs Micronized By Crystallization From Supercritical Gases", by H. Loth et al., International Journal of Pharmaceutics, vol. 32, 1986, pp. 265-267.
H. Sekikawa et al., Chem. Pharm. Bull., vol 26, pp. 3033-3039 (1978).
Nature, vol. 193, pp. 588-589 (1962).
N. Kaneniwa et al., Chem. Pharm. Bull., vol. 23, pp. 2973-2986 (1975).
Yakugaku Zasshi, vol. 101, No. 8, pp. 723-732 (1981).

Primary Examiner—T. K. Page

[57] ABSTRACT

A process for micronizing a slightly-soluble drug characterized by subjecting a mixture of said drug and a sugar or sugar alcohol to high-speed stirring comminution or impact comminution in order to produce a micronized drug having an average diameter of less than about 2-3 mm. Also provided is a pharmaceutical formulation which comprises the micronized drug.

7 Claims, No Drawings

PROCESS FOR MICRONIZING SLIGHTLY-SOLUBLE DRUG

BACKGROUND OF THE INVENTION

1. Field of the Invention

The present invention relates to a process for micronizing a slightly-soluble drug. More specifically, it relates to a process for micronizing a slightly-soluble drug, which comprises grinding said drug in the presence of a sugar or sugar alcohol of a lower molecular weight as a grinding aid, and to a pharmaceutical formulation containing the resultant ultrafine drug as an active ingredient.

2. Description of the Related Arts

When a pharmaceutical formulation containing a drug is orally administered to subjects, a dissolution step is essential for the drug to be absorbed through gastrointestinal tract. It has long been recognized that a slightly-soluble drug often shows insufficient bioavailability because of the poor solubility in gastrointestinal fluids, which compels said drug to pass through the site of absorption before it completely dissolves in the fluids. Various attempts have been made from the aspect of pharmaceutics to improve and increase the absorption efficiency of a slightly-soluble drug in gastrointestinal tract.

Specific examples of said attempts employed for preparing improved formulations include following countermeasures.

1) Providing a soft gelatin capsule containing a solution of said drug in a nonaqueous solvent.
2) Providing a water-soluble salt of said drug.
3) Providing a solid solution which is prepared by dissolving the drug with a suitable polymer in an organic solvent and drying the solution promptly (see, reference 1 listed at the end of this specification).
4) A drug is dissolved in an organic solvent and adsorbed on a porous material in the form of ultrafine particles so that the surface area may be increased.
5) A drug is pulverized in the presence of an appropriate adduct to obtain an amorphous powder (see, references 3, 4 and 5).
6) A drug is just ground into a fine powder (see, reference 2).

The above countermeasures 1) to 5) are associated with alteration of properties of a drug in molecular level. These countermeasures, although advantageous in some aspects, have several disadvantages described below.

In the method of the above item 1), it is not always easy to find out a suitable nonaqueous solvent. In addition, the capsule size may become too big for oral administration. Furthermore, the production cost may be high.

The second method of the above item 2, where the drug is converted into a water-soluble salt, is not applicable to all kinds of drugs because many drugs may not form such salts. Additionally, formation of a water-soluble salt may be often accompanied by alteration of pharmaceutical activity of the drug and/or decrease its stability. Therefore, this method is just applicable to limited drugs.

The methods of the above items 3 and 4 are not applicable to every drug and the methods require the use of organic solvents which may be harmful to living bodies. Production cost may also be high in these methods.

In the method of the above item 5, a slightly-soluble drug is mixed with an adduct such as (1) $\beta$-1,4-glucan, (2) adsorbent, or (3) polyvinylpyrrolidone. The drug is pulverized in the presence of such adduct to obtain the drug in the form of amorphous powder which may exhibit improved dissolution rate and bioavailability. However, the amorphous form is not physically stable and often converted reversibly to more stable crystal form. Consequently, the dispersion or dissolution properties of the drug may be changed as time passes.

The method of the above item 6) differs from those of items 1) to 5) which all change the properties of a drug in molecular level, in that the former contemplates to improve bioavailability of a drug through micronization. The micronization has the following advantages.

a) The alteration of crystal form of a drug is slight or moderate;
b) The operation is safe because no organic solvent is employed;
c) The production cost is low; and
d) The operation is easy.

In general, a milling process (it is also referred to as grinding, pulverization, and the like) is essential in the process of the production of pharmaceutical formulations. Examples of mills commonly used involve dry-type mills, such as jet, ball, vibration, and hammer mill. These dry-type mills are used to grind a drug alone to afford particles of several $\mu m$ in diameter. However, it is difficult to obtain finer particles by conventional means. Especially, preparation of submicron particles of less than 1 $\mu m$ in diameter is almost impossible.

This difficulty is associated with peculiar nature inherent to micronized particles that such particles have a tendency to aggregate, adhere, or solidify as the particle size decreases. Thus, it is extremely difficult to grind a drug into ultrafine particles having a diameter of less than several $\mu m$ by conventional milling procedures. Accordingly, a practically applicable process for preparing ultrafine particles of a drug has long been needed.

SUMMARY OF THE INVENTION

The present inventors have found that ultrafine particles of a slightly-soluble drug, whose average diameter is less than about 2 to 3 $\mu m$, preferably less than 1 $\mu m$, can be easily obtained by grinding the drug in the presence of a grinding aid selected from a sugar and a sugar alcohol by means of a high-speed stirring mill or impact mill.

Accordingly, in one aspect, this invention provides a process for micronizing slightly-soluble drug characterized by subjecting a mixture of said drug and a sugar or sugar alcohol to high-speed stirring comminution or impact comminution.

This invention also provides a pharmaceutical formulation which comprises, as an active ingredient, a micronized drug produced according to the above process together with suitable excipients or diluents therefor.

DETAILED DESCRIPTION OF THE INVENTION

The term "slightly-soluble drug" herein used refers to a pharmaceutical compound which dissolves in water, particularly at 20° C., at the ratio of 5 mg/ml or less and which is insufficiently absorbed at gastrointestinal tract when it is administered in the form of conventional solid formulations. Specific examples of the slightly-soluble drugs are coronary vasodilators such as nifedipine, nicardipine, nimodipine, dipyridamole, disopyramide, prenylamine lactate, and efloxate; antihypertensives such as dihydroergotoxine and prazosin; steroidal anti-inflammatory agents such as cortisone, dexamethasone, betamethasone, and fluocinolone acetonide; non-steroidal anti-inflammatory agents such as indomethacin, naproxen, and ketoprofen; psychoneurotic agents such as phenytoin, phenacemide, ethylphenacemide, ethotoin, primidone, phensuximide, diazepam, nitrazepam, and clonazepam; cardiacs such as digoxin, digitoxin, and ubidecarenon; diuretics such as spironolactone, triamterene, chlorthalidone, polythiazide, and benzthiazide; chemotherapeutics such as griseofulvin, nalidixic acid, and chloramphenicol; skeletal muscle relaxants such as chlorzoxazone, phenprobamate, and carisoprodol; anticonvulsants such as etomidoline; antihistaminic agents such as diphenhydramine, promethazine, mequitazine, bisbenthiamine, and clemastine fumarate.

Sugars and sugar alcohols used as a grinding aid are selected from pharmaceutically acceptable sugars and sugar alcohols having no influence on the medical effects of an active ingredient. For the purpose of the invention, it is preferable to use sugars or sugar alcohols having a molecular weight of less than 500, and capable of easily dispersing and dissolving in water, whereby improving dissolution rate of the active ingredient. Examples of sugars and sugar alcohols usable in the present invention include xilitol, mannitol, solbitol, arabinose, ribose, xylose, glucose, mannose, galactose, sucrose, lactose, and the like. They can be used alone, or as a mixture of two or more of these compounds. The most preferable sugar is mannitol.

In the process of the invention, one part by weight of an active ingredient is combined with about 2.5 to about 50 parts, preferably about 2.5 to about 20 parts, more preferably about 5 to about 10 parts by weight, of a sugar.

Mills employable in the present process are, for example, dry mills capable of grinding a material into ultrafine particles through a mechanical impact and/or attrition, which are called high-speed stirring mills and impact mills. Specific examples of the preferred mills are cylinder-type mills such as rotating ball mill, vibrating ball mill, tube mill, rod mill, and the like.

The time required for the completion of the present process depends on the properties of the drug and sugar or sugar alcohol, function of the mill, content of the sugar or sugar alcohol in the mixture, and total amount of the mixture to be treated. The grinding time may also be changed according to the strength of impact, and it is generally between 5 to 30 minutes under a strong impact, while it is between 8 to 100 hours under a weak impact. The drug and sugar or sugar alcohol can be used in the present procedure without pre-treatment, but they can be coarsely ground before use.

The mixture which have undergone micronizing treatment according to the process of the present invention contains ultrafine particles of the drug having an average diameter of less than 1 μm. Co-existence of the sugar or sugar alcohol in the mixture after the treatment is advantageous because it has high solubility in water and can disperse into water, whereby increasing dissolution rate of the drug.

The mixture treated according to the process of the invention can be used as such for the preparation of pharmaceutical compositions. Alternatively, after dispersing the mixture into water, the resulting suspension can be subjected to ultrafiltration to remove the sugar or sugar alcohol and subsequently dried to yield a micronized slightly-soluble drug in high purity.

The micronized drug obtained by the invention can be formulated in the form of powders, tablets, granules, capsules, aerosols, suspensions, syrups, ointments, suppositories, and the like, with one or more pharmaceutically acceptable excipients and/or diluents.

The following examples further illustrate the present invention. The examples are not intended to be limiting the scope of the invention in any respect and should not be so construed.

EXAMPLE 1

Micronization of Naproxene in the Presence of D-Mannitol

Naproxene (1 g), a slightly-soluble pharmaceutical compound, was mixed with D-mannitol (9 g, Katayama Chemicals, Ltd.). The mixture was then ground for one hour in a sealed stainless steel vibrational ball mill (Specks, Co., volume: 50 ml) with the aid of two stainless steel balls of 9 mm in diameter.

The size distribution of naproxene in the resultant micronized product was determined in the following manner:

The product obtained above (sample 1), a mixture of separately ground naproxene and D-mannitol (control 1), and naproxene powder (untreated raw material) (control 2) were employed in the experiment. The measurement was conducted using a centrifugal particle size analyzer (SA-CP2, Shimazu Seisakusyo, Japan). The 50% average diameter of naproxene was determined on the basis of volume. The results are shown below:

| Sample | 50% average diameter of naproxene |
| --- | --- |
| Sample 1 | 0.32 μm |
| Control 1 | 4.4 μm |
| Control 2 | 19 μm |

The influence of the duration of treating time on the particle size was investigated, and it was found that the size was reduced rapidly in the initial stage and almost reached to equilibrium within 30 minutes.

EXAMPLE 2

Micronization of Various Slightly-Soluble Drugs in the Presence of D-mannitol

Slightly-soluble pharmaceutical compounds (each 1 g) were subjected to the micro-grinding procedure as described in Example 1 in the presence of D-mannitol (9 g, Katayama Chemicals, Ltd.) (60 minutes, mixing ratio of 1:9).

The size distribution of the each compound was determined and the 50% average diameter thereof was obtained in the same manner as above. For comparison, each pharmaceutical compound was ground alone. Experimental results are shown in Table 1 below.

TABLE 1

Particle Sizes of Various Compounds Micronized in the Presence of D-mannitol

| | 50% Average Diameter (μm) | | |
| --- | --- | --- | --- |
| | Before Milling | After Milling alone | After Milling mixture |
| compound | | | |
| indomethacin | 9 | 1.3 | 0.35 |
| phenytoin | 32 | 2.7 | 0.27 |

TABLE 1-continued

Particle Sizes of Various Compounds Micronized in the Presence of D-mannitol

| compound | 50% Average Diameter (μm) | | |
| --- | --- | --- | --- |
| | Before Milling | After Milling alone | mixture |
| naproxene | 19 | 4.4 | 0.32 |
| bisbentiamine | 12 | 2.6 | 0.42 |
| chloramphenichol | 67 | 22.0 | 0.53 |
| griseofulvin | 6 | 14.0 | 0.26 |
| oxophosphoric acid | 7 | 3.4 | 0.1 |

Table 1 shows that the particle size of each micronized compound is less than 1 μm and that the micronizing process of the invention gives ultrafine particles compared with those obtained by grinding without D-mannitol.

EXAMPLE 3

Micronization of Oxophosphoric Acid in the Presence of Various Sugars or Sugar Alcohols Oxophosphric acid (1 g), a slightly-soluble pharmaceutical compound, was subjected to the micronizing process as described in Example 1 in the presence of each of various sugars (each 9 g) (60 minutes, mixing ratio of 1:9).

The size distribution of oxophosphoric acid was determined and the 50% average diameter thereof was obtained in the same manner as above. As a control, oxophosphoric acid was ground alone. Test results are shown in Table 2 below.

TABLE 2

| Particle Sizes of Micronized Oxophosphoric Acid | |
| --- | --- |
| Sugars | 50% average diameter (μm) |
| None | 3.4 |
| glucose | 0.22 |
| lactose | 0.22 |
| sucrose | 0.22 |
| maltose | 0.19 |
| xilitol | 0.21 |
| sorbitol | 0.22 |
| D-mannitol | 0.15 |

Table 2 shows that all of the listed sugars are effective to give a micronized oxophsphoric acid having a particle size of less than 1 μm. It can be seen that D-mannitol is the most efficient sugar among others.

EXAMPLE 4

Isolation of Micronized Oxophosphoric Acid

To the micronized product comprising oxophosphoric acid and D-mannitol (10 g, prepared in Example 3) was added a distilled water (100 ml), and the mixture was stirred in order to disperse the acid and also to dissolve mannitol. The resultant suspension was charged in Ultrafiltration System ( Model UHP-62 Toyo Paper, Japan, equipped with a ultrafilter UK-50, 50,000-molecular weight cutoff), and ultrafiltered under pressure to remove dissolved D-mannitol. After the addition of distilled water (100 ml), the ultrafiltration was repeated under pressure with stirring. The solid residue left on the ultrafilter membrane was recovered and dried over phosphorus pentaoxide under reduced pressure for 24 hours at 50° C. to obtain oxophosphoric acid as a ultrafine powder with high purity (purity≧98%). Scanning electron microscope observation revealed that it consisted of particles in the form of fine prismatic crystals having an average diameter of from about 0.1 to 0.4 μm.

The above test shows that the micronized oxophosphoric acid can be purified by subjecting the product to dispersing, ultrafiltering, and drying treatments.

EXAMPLE 5

Micronization of Phenytoin

A mixture of phenytoin (10 g) and D-mannitol (90 g) was ground in a ceramic ball mill (volume: 1L; 90 ceramic balls of 20 mm in diameter) at 120 rpm for 48 hours. Size distribution measurement was carried out in the same manner as Example 1 and the 50% average diameter was determined. The 50% average diameter of phenytoin before grinding was 3.2 μm, while it was 0.6 μm after grinding.

The influence of the duration of treating time on the particle size was investigated, and it was found that the size was reduced rapidly in the initial stage and almost reached to equilibrium within 48 hours. Further grinding up to 200 hours gave no change in the particle size.

The following formulation examples are illustrative only and are not intend to limit the scope of the invention.

FORMULATION 1

Suspension Syrups

To a micronized product consisting of chloramphenicol (10 g) and sucrose (90 g) prepared according to the procedure described in Example 4 were added methyl celulose and water, and the mixture was homogenized in a homomixer to obtain a suspension syrup of chloramphenycol.

The average diameters of chloramphenycol particles before and after the micronization, and just after formulation to the suspension syrup, were determined according to the procedure described in Example 1. Average diameter of the particles was 10 μm before micronization, and 0.6 μm after micronization. In suspension syrup, the average diameter of the particles was 0.7 μm when measured immediately after the preparation, and the size remained unchanged after keeping the syrup at room temperature. The test results show that formulation procedure gives no adverse effect to the micronized product, and a stable suspension syrup of chloramphenycol can be obtained while keeping the particle size constant.

FORMULATION 2

Tablets

To a micronized product consisting of griseofulvin and D-mannitol (prepared in Example 2) were added corn starch as a disintegrator and polyvinylpyrrolidone as a binder. The mixture was subjected to a wet granulation. Granules so produced were mixed with magnesium stearate, and the mixture was compressed by means of a tablet machine to yield tablets. The tablets were completely disintegrated in water within 10 minutes when subjected to disintegration test described in the 11th revised edition of Japanese pharmacopoeia. After the disintegration test, size distribution of griseofulvin in the solution was measured by scanning electron micrographic method. The average diameter of griseofulbin in the solution was 0.4 μm.

FORMULATION 3

Granules

Micronized product consisting of oxophosphoric acid and D-mannitol (prepared in Example 2) was admixed with hydroxypropyl cellulose as a binder. The mixture was granulated using a rotary granulator and dried to yield granules. The granules were completely disintegrated in water within 10 minutes when subjected to disintegration test described in the 11th revised edition of Japanese pharmacopoeia. After the disintegration test, size distribution of oxophosphoric acid in the solution was measured in the manner as in Example 1. The average diameter of oxophosphoric acid in the solution was 0.3 μm.

REFERENCES

1. H. Sekikawa, et al., Chem.Pharm.Bull., vol.26, 3033 (1978)
2. R. M. Atkinson, et al., Nature, vol.193, 588 (1962)
3. Y. Nakai, Japanese Patent Publication (kokai) No. 51-32718, and K. Takeo, et al., Japanese Patent Publication (kokai) No. 53-9315
4. M. Matsui, et al., Japanese Patent Publication (kokai) No. 60-8220
5. N. Kaneniwa, et al., Chem.Pharm.Bull., vol.23, 2986 (1975)
6. K. Kigasawa, et al., Yakugaku-Zasshi, vol. 101(8), 723–732 (1981)

What is claimed is:

1. A process for micronizing a slightly-soluble drug comprising subjecting a mixture of said drug and a sugar or sugar alcohol, the weight ratio of said sugar or sugar alcohol being at least 2.5 or more parts by weight to one part by weight of the drug, to high-speed stirring comminution or impact comminution to give a micronized drug having an average diameter of less than 1 μm.

2. The process of claim 1, wherein the molecular weight of the sugar or sugar alcohol is less than 500.

3. The process of claim 1 or 2, wherein the sugar or sugar alcohol is selected from the group consisting of xylitol, mannitol, sorbitol, arabinose, ribose, xylose, glucose, mannose, galactose, sucrose and lactose.

4. A pharmaceutical formulation which comprises, as an active ingredient, a micronized drug produced according to claim 1 together with suitable excipients or diluents therefor.

5. The process according to claim 1, wherein said weight ratio of sugar or sugar alcohol is about 2.5 to about 50 parts by weight to one part by weight of the drug.

6. The process according to claim 5, wherein said weight ratio of sugar or sugar alcohol is about 2.5 to about 20 parts by weight to one part by weight of the drug.

7. The process according to claim 6, wherein said weight ratio of sugar or sugar alcohol is about 5 to about 10 parts by weight to one part by weight of the drug.

* * * * *